US011957791B2

(12) United States Patent
Li et al.

(10) Patent No.: US 11,957,791 B2
(45) Date of Patent: Apr. 16, 2024

(54) METHODS

(71) Applicant: INTRA-CELLULAR THERAPIES, INC., New York, NY (US)

(72) Inventors: Peng Li, New Milford, NJ (US); Robert Davis, San Diego, CA (US); William Paul Findlay, Massapequa, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 174 days.

(21) Appl. No.: 17/270,573

(22) PCT Filed: Aug. 30, 2019

(86) PCT No.: PCT/US2019/049061
§ 371 (c)(1),
(2) Date: Feb. 23, 2021

(87) PCT Pub. No.: WO2020/047407
PCT Pub. Date: Mar. 5, 2020

(65) Prior Publication Data
US 2021/0220280 A1 Jul. 22, 2021

Related U.S. Application Data

(60) Provisional application No. 62/779,920, filed on Dec. 14, 2018, provisional application No. 62/725,944, filed on Aug. 31, 2018.

(51) Int. Cl.
A61K 9/20 (2006.01)
A61K 9/28 (2006.01)
A61K 31/4985 (2006.01)

(52) U.S. Cl.
CPC .......... A61K 9/2013 (2013.01); A61K 9/2009 (2013.01); A61K 9/2054 (2013.01); A61K 9/284 (2013.01); A61K 31/4985 (2013.01); C07B 2200/13 (2013.01)

(58) Field of Classification Search
CPC .... A61K 31/4985; A61K 9/0053; A61K 9/16; A61K 9/4825; A61K 9/485; A61K 9/4858; A61K 9/4891; A61K 9/14; A61K 9/1605; A61K 9/1611; A61K 9/1652; A61K 9/141; A61K 9/20; A61K 9/2004; A61K 9/2009; A61K 9/2013; A61K 9/2018; A61K 9/2036; A61K 9/2077
See application file for complete search history.

(56) References Cited

U.S. PATENT DOCUMENTS

| 1,960,534 A | 5/1934 | Gibney |
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,001,263 A | 1/1977 | Plattner et al. |
| 4,115,577 A | 9/1978 | Rajagopalan |
| 4,136,145 A | 1/1979 | Fuchs et al. |
| 4,183,936 A | 1/1980 | Rajagopalan |
| 4,219,550 A | 8/1980 | Rajagopalan |
| 4,238,607 A | 12/1980 | Rajagopalan |
| 4,389,330 A | 6/1983 | Tice et al. |
| 4,522,944 A | 6/1985 | Doria et al. |
| 4,530,840 A | 7/1985 | Tice et al. |
| 4,849,246 A | 7/1989 | Schmidt |
| 4,971,971 A | 11/1990 | Tokunaga et al. |
| 4,985,432 A | 1/1991 | Tokunaga et al. |
| 5,114,976 A | 5/1992 | Norden |
| 5,151,419 A | 9/1992 | Perenyi et al. |
| 5,538,739 A | 7/1996 | Bodmer et al. |
| 5,576,460 A | 11/1996 | Buchwald et al. |
| 5,629,003 A | 5/1997 | Horstmann et al. |
| 5,648,539 A | 7/1997 | Goodbrand |
| 5,648,542 A | 7/1997 | Goodbrand et al. |
| 5,654,482 A | 8/1997 | Goodbrand |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,763,476 A | 6/1998 | Delbressine et al. |
| 5,834,493 A | 11/1998 | Gil Quintero et al. |
| 5,847,166 A | 12/1998 | Buchwald et al. |
| 5,902,901 A | 5/1999 | Goodbrand et al. |
| 5,948,430 A | 9/1999 | Zerbe et al. |
| 6,043,370 A | 3/2000 | Kubo et al. |
| 6,166,226 A | 12/2000 | Buchwald et al. |
| 6,221,335 B1 | 4/2001 | Foster |
| 6,235,936 B1 | 5/2001 | Buchwald et al. |
| 6,307,087 B1 | 10/2001 | Buchwald et al. |
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,440,710 B1 | 8/2002 | Keinan et al. |
| 6,448,243 B1 | 9/2002 | Kitazawa et al. |
| 6,465,693 B2 | 10/2002 | Buchwald et al. |
| 6,541,639 B2 | 4/2003 | Zhou et al. |
| 6,544,559 B2 | 4/2003 | Mesens et al. |

(Continued)

FOREIGN PATENT DOCUMENTS

| EP | 0 058 481 | 8/1982 |
| EP | 0 856 508 | 8/1998 |

(Continued)

OTHER PUBLICATIONS

"Study of a Novel Antipsychotic ITI-007 in Schizophrenia," Clinical Trials.gov, 6 pages, Dec. 26, 2011.

(Continued)

Primary Examiner — Micah Paul Young
(74) Attorney, Agent, or Firm — Hoxie & Associates LLC

(57) ABSTRACT

The present disclosure relates to solid oral dosage forms comprising lumateperone, in free, or pharmaceutically acceptable salt form, optionally in combination with one or more additional therapeutic agents, processes for manufacture thereof and methods of use in the treatment or prophylaxis of disease.

17 Claims, No Drawings

(56) References Cited

U.S. PATENT DOCUMENTS

| | | |
|---|---|---|
| 6,548,493 B1 | 4/2003 | Robichaud et al. |
| 6,552,017 B1 | 4/2003 | Robichaud et al. |
| 6,552,024 B1 | 4/2003 | Chen et al. |
| 6,603,008 B1 | 8/2003 | Ando et al. |
| 6,699,852 B2 | 3/2004 | Robichaud et al. |
| 6,713,471 B1 | 3/2004 | Robichaud et al. |
| 6,759,554 B2 | 7/2004 | Buchwald et al. |
| 6,762,329 B2 | 7/2004 | Marcoux et al. |
| 6,828,314 B2 | 12/2004 | Frank et al. |
| 6,849,619 B2 | 2/2005 | Robichaud et al. |
| 6,849,640 B2 | 2/2005 | Ennis et al. |
| 6,867,298 B2 | 3/2005 | Buchwald et al. |
| 6,884,429 B2 | 4/2005 | Koziak et al. |
| 6,888,032 B2 | 5/2005 | Buchwald et al. |
| 6,946,560 B2 | 9/2005 | Buchwald et al. |
| 7,026,498 B2 | 4/2006 | Buchwald et al. |
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,879 B2 | 5/2007 | Buchwald et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,462,641 B2 | 12/2008 | Igo et al. |
| 7,517,990 B2 | 4/2009 | Ito et al. |
| 7,592,454 B2 | 9/2009 | Lee et al. |
| 7,614,727 B2 | 11/2009 | Hori |
| 7,645,752 B2 | 1/2010 | McDevitt et al. |
| 7,998,971 B2 | 8/2011 | Barlow et al. |
| 8,309,722 B2 | 11/2012 | Tomesch et al. |
| 8,414,922 B2 | 4/2013 | Bryson et al. |
| 8,461,148 B2 | 6/2013 | Hollander |
| 8,598,119 B2 | 12/2013 | Mates et al. |
| 8,603,514 B2 | 12/2013 | Yang et al. |
| 8,648,077 B2 | 2/2014 | Tomesch et al. |
| 8,652,378 B1 | 2/2014 | Yang et al. |
| 8,697,700 B2 | 4/2014 | Surman et al. |
| 8,779,139 B2 | 7/2014 | Tomesch et al. |
| 8,791,138 B2 | 7/2014 | Seeman et al. |
| 8,835,459 B2 | 9/2014 | Kottayil et al. |
| 8,900,497 B2 | 12/2014 | Yang et al. |
| 8,900,498 B2 | 12/2014 | Yang et al. |
| 8,906,277 B2 | 12/2014 | Yang et al. |
| 8,993,572 B2 | 3/2015 | Mates et al. |
| 9,108,340 B2 | 8/2015 | Yang et al. |
| 9,168,258 B2 | 10/2015 | Mates et al. |
| 9,199,995 B2 | 12/2015 | Tomesch et al. |
| 9,216,175 B2 | 12/2015 | Amancha et al. |
| 9,315,504 B2 | 4/2016 | Tomesch et al. |
| 9,371,324 B2 | 6/2016 | Mates et al. |
| 9,393,192 B2 | 7/2016 | Yam et al. |
| 9,427,412 B2 | 8/2016 | Bryson et al. |
| 9,567,327 B2 | 2/2017 | Xiong et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,077,267 B2 | 9/2018 | Mates et al. |
| 10,117,867 B2 | 11/2018 | Mates et al. |
| 10,221,176 B2 | 3/2019 | Tomesch et al. |
| 10,322,134 B2 | 6/2019 | Vanover et al. |
| 10,464,938 B2 | 11/2019 | Tomesch et al. |
| 10,597,395 B2 | 3/2020 | Tomesch et al. |
| 10,688,097 B2 | 6/2020 | Yao et al. |
| 10,695,345 B2 * | 6/2020 | Li .......................... A61P 25/18 |
| 10,702,522 B2 | 7/2020 | Mates et al. |
| 10,716,786 B2 | 7/2020 | Li et al. |
| 10,844,061 B2 | 11/2020 | Li et al. |
| 10,960,009 B2 | 3/2021 | Vanover et al. |
| 10,960,010 B2 | 3/2021 | Vanover et al. |
| 11,026,951 B2 | 6/2021 | Mates et al. |
| 11,052,084 B2 * | 7/2021 | Li .......................... A61K 9/4858 |
| 2001/0008942 A1 | 7/2001 | Buchwald et al. |
| 2001/0036472 A1 | 11/2001 | Wong et al. |
| 2002/0155154 A1 | 10/2002 | Wong et al. |
| 2003/0065187 A1 | 4/2003 | Buchwald et al. |
| 2004/0019216 A1 | 1/2004 | Buchwald et al. |
| 2004/0034015 A1 | 2/2004 | Robichaud et al. |
| 2004/0085699 A1 | 5/2004 | Anthony |
| 2004/0092534 A1 | 5/2004 | Yam et al. |
| 2004/0122226 A1 | 6/2004 | Ghosh et al. |
| 2004/0127482 A1 | 7/2004 | Robichaud et al. |
| 2004/0138468 A1 | 7/2004 | Buchwald et al. |
| 2004/0142970 A1 | 7/2004 | Chung et al. |
| 2004/0180875 A1 | 9/2004 | Lee et al. |
| 2004/0186136 A1 | 9/2004 | Alken et al. |
| 2004/0209864 A1 | 10/2004 | Robichaud et al. |
| 2004/0220178 A1 | 11/2004 | Robichaud et al. |
| 2005/0166771 A1 | 8/2005 | Gygi et al. |
| 2005/0215794 A1 | 9/2005 | Buchwald et al. |
| 2005/0222209 A1 | 10/2005 | Zeldis et al. |
| 2005/0222238 A1 | 10/2005 | Alken |
| 2005/0248900 A1 | 11/2005 | Anthony |
| 2005/0250959 A1 | 11/2005 | Buchwald et al. |
| 2006/0148808 A1 | 7/2006 | Robichaud et al. |
| 2006/0178362 A1 | 8/2006 | Robichaud et al. |
| 2006/0205787 A1 | 9/2006 | Muller et al. |
| 2006/0264673 A1 | 11/2006 | Buchwald et al. |
| 2007/0049759 A1 | 3/2007 | Ghosh et al. |
| 2007/0066677 A1 | 3/2007 | Igo et al. |
| 2007/0082929 A1 | 4/2007 | Gant et al. |
| 2007/0197695 A1 | 8/2007 | Potyen et al. |
| 2007/0203120 A1 | 8/2007 | McDevitt et al. |
| 2008/0069885 A1 | 3/2008 | Mesens et al. |
| 2008/0132552 A1 | 6/2008 | Kleinman et al. |
| 2008/0194592 A1 | 8/2008 | Mates et al. |
| 2008/0249082 A1 | 10/2008 | Hollander |
| 2008/0280941 A1 | 11/2008 | Lourtie |
| 2008/0303137 A1 | 12/2008 | Ward et al. |
| 2009/0076159 A1 | 3/2009 | Czarnik |
| 2009/0209608 A1 | 8/2009 | Czarnik |
| 2010/0113781 A1 | 5/2010 | Tomesch et al. |
| 2010/0159033 A1 | 6/2010 | Gant et al. |
| 2011/0020369 A1 | 1/2011 | De Wall Malefyt et al. |
| 2011/0071080 A1 | 3/2011 | Mates et al. |
| 2011/0112105 A1 * | 5/2011 | Tomesch ................ A61P 25/24 514/250 |
| 2011/0269777 A1 | 11/2011 | Bachurin et al. |
| 2012/0196814 A1 | 8/2012 | Gong et al. |
| 2013/0046097 A1 | 2/2013 | Tomesch et al. |
| 2013/0202692 A1 | 8/2013 | Mates et al. |
| 2014/0050783 A1 * | 2/2014 | Mates ................ A61K 9/0053 514/250 |
| 2014/0088083 A1 | 3/2014 | Hollander |
| 2014/0210117 A1 | 7/2014 | Friesen et al. |
| 2014/0323491 A1 | 10/2014 | Tomesch et al. |
| 2014/0364609 A1 | 12/2014 | Tomesch et al. |
| 2015/0004237 A1 | 1/2015 | Edgar et al. |
| 2015/0031804 A1 | 1/2015 | Shiramizu et al. |
| 2015/0038519 A1 | 2/2015 | Mates et al. |
| 2015/0072964 A1 * | 3/2015 | Mates ..................... A61P 43/00 514/217 |
| 2015/0079172 A1 | 3/2015 | Mates et al. |
| 2015/0080404 A1 | 3/2015 | Mates et al. |
| 2015/0166540 A1 | 6/2015 | Mates et al. |
| 2016/0031885 A1 | 2/2016 | Li et al. |
| 2016/0194325 A1 | 7/2016 | Tomesch et al. |
| 2016/0194326 A1 | 7/2016 | Tomesch et al. |
| 2016/0235720 A1 | 8/2016 | Foster et al. |
| 2016/0310502 A1 | 10/2016 | Vanover et al. |
| 2016/0354315 A1 * | 12/2016 | Li .......................... A61K 9/2027 |
| 2017/0037048 A1 | 2/2017 | Mates et al. |
| 2017/0114037 A1 | 4/2017 | Davis et al. |
| 2017/0183350 A1 | 6/2017 | Mates et al. |
| 2017/0189398 A1 | 7/2017 | Mates et al. |
| 2017/0283417 A1 | 10/2017 | Li et al. |
| 2018/0044337 A1 | 2/2018 | Tomesch et al. |

(56) References Cited

U.S. PATENT DOCUMENTS

| | | |
|---|---|---|
| 2018/0200256 A1 | 7/2018 | Vanover et al. |
| 2019/0062334 A1 | 2/2019 | Mates et al. |
| 2019/0071445 A1 | 3/2019 | Li et al. |
| 2019/0112310 A1 | 4/2019 | Li et al. |
| 2019/0183888 A1 | 6/2019 | Mates et al. |
| 2019/0211015 A1 | 7/2019 | Mittelman et al. |
| 2019/0218219 A1 | 7/2019 | Tomesch et al. |
| 2019/0231780 A1 | 8/2019 | Yao et al. |
| 2019/0290655 A1 | 9/2019 | Vanover et al. |
| 2019/0292185 A1 | 9/2019 | Tomesch et al. |
| 2019/0298730 A1 | 10/2019 | Vanover et al. |
| 2019/0328745 A1 | 10/2019 | Vanover et al. |
| 2019/0388418 A1 | 12/2019 | Li |
| 2020/0017499 A1 | 1/2020 | Mates et al. |
| 2020/0087305 A1 | 3/2020 | Tomesch et al. |
| 2020/0102304 A1 | 4/2020 | Li et al. |
| 2020/0102310 A1 | 4/2020 | Li et al. |
| 2020/0115380 A1 | 4/2020 | Tomesch et al. |
| 2020/0157100 A1 | 5/2020 | Li |
| 2020/0392135 A1 | 12/2020 | Wennogle et al. |
| 2020/0405713 A1 | 12/2020 | Mates et al. |
| 2020/0407362 A1 | 12/2020 | Mates et al. |
| 2021/0002280 A1 | 1/2021 | Mates et al. |
| 2021/0032247 A1 | 2/2021 | Li et al. |

FOREIGN PATENT DOCUMENTS

| | | | | |
|---|---|---|---|---|
| EP | 0 976 732 | 2/2000 | | |
| EP | 1 245 553 | 10/2002 | | |
| EP | 1 254 884 | 11/2002 | | |
| EP | 1 539 115 | 6/2005 | | |
| EP | 1 564 671 | 8/2005 | | |
| GB | 1476087 | 6/1977 | | |
| GB | 2145422 | 3/1985 | | |
| RU | 2465267 | 10/2012 | | |
| WO | WO 1995/013814 | 5/1995 | | |
| WO | WO 1995/026325 | 10/1995 | | |
| WO | WO 1999/043643 | 9/1999 | | |
| WO | WO 2000/002887 | 1/2000 | | |
| WO | WO 2000/048610 | 8/2000 | | |
| WO | WO 2000/064899 | 11/2000 | | |
| WO | WO 2000/077001 | 12/2000 | | |
| WO | WO 2000/077002 | 12/2000 | | |
| WO | WO 2000/077010 | 12/2000 | | |
| WO | WO 2002/059129 | 8/2002 | | |
| WO | WO 2003/014118 | 2/2003 | | |
| WO | WO 2004/064738 | 8/2004 | | |
| WO | WO 2005/030214 | 4/2005 | | |
| WO | WO 2006/081332 | 8/2006 | | |
| WO | WO 2014/110322 | 7/2014 | | |
| WO | WO 2017/117514 | 7/2017 | | |
| WO | WO-2018031535 A1 * | 2/2018 | ........... | C07C 309/30 |
| WO | WO 2018/106916 | 6/2018 | | |
| WO | WO-2018189646 A1 * | 10/2018 | ........... | A61K 31/519 |
| WO | WO 2019/102240 | 5/2019 | | |

OTHER PUBLICATIONS

Alvir, et al., "Clozapine-Induced Agranulocytosis," *The New England Journal of Medicine*, vol. 329, No. 3, pp. 162-167, (1993).

Angst et al. "Prevalence and Characteristics of Undiagnosed Bipolar Disorders in Patients With a Major Depressive Episode", *Arch Gen Psychiatry*, vol. 68, No. 8, pp. 701-709, (2011).

Baille, T.A., "The Use of Stable Isotopes in Pharmacological Research," *Pharmacol. Reviews*, vol. 33, No. 2, pp. 81-132, (1981).

Balbach, et al. "Pharmaceutical evaluation of early development candidates 'the 100 mg-approach", International Journal of Pharmaceutics, vol. 275, pp. 1-12 (2004).

Bastin, "Salt Selection and Optimized Procedures for Pharmaceutical New Chemical Entities", Organic Process and Research Development, vol. 4, No. 5, pp. 427-435 (2000).

Bechtold, D.A., et al., "Circadian Dysfunction in Disease," Trends in Pharmacological Sciences,31(5): 191-198, (2010); Abstract.

Bennett, et al., "Cecil Textbook of Medicine," 20th Edition, vol. 1, pp. 1004-1010, (1996).

Borghans et al., "Animal Models for Posttraumatic Stress Disorder: An Overview of What is Used in Research," *World J. Psychiatr.*, vol. 5, No. 4, pp. 387-396, (2015); DOI: 10.5498/wjp.v5.i4.387.

Bremner, et al., "Neuroimaging of Posttraumatic Stress Disorder", Psychiatric Annals Journal, vol. 28, No. 8, p. 445-450, (1998).

Browne, T.R., "Stable Isotope Techniques in Early Drug Development: An Economic Evaluation," J. Clin. Pharmacol., vol. 38, pp. 213-220, (1998).

Bryan-Lluka, et al., "Potencies of Haloperidol Metabolites as Inhibitors of the Human Noradrenaline, Dopamine and Serotonin Transporters in Transfected COS-7 Cells," Naunyn-Shemiedeberg's Arch Pharmacol, vol. 360, pp. 109-115, (1999).

Byrn, "Pharmaceutical Solids: A Strategic Approach to Regulatory Considerations", vol. 12, No. 7, p. 945-954 (1995).

Caira, M.R., "Crystalline Polymorphism of Organic Compounds," Topics in Current Chemistry, vol. 198, p. 163-203, (1998).

Cherrah, et al., "Study of Deuterium Isotope Effects on Protein Binding by Gas Chromatography/Mass Spectrometry. Caffeine and Deuterated Isotopomers," Biomedical and Environmental Mass Spectrometry, vol. 14, pp. 653-657, (1987).

Darmani, et al., "Do Functional Relationships Exist Between 5-HT1A and 5-HT2 Receptors?" Pharmacology and Biochemistry & Behavior, vol. 36, pp. 901-906, (1990).

Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).

Davis, et al., "ITI-007 demonstrates brain occupancy at serotonin 5-HT2A and dopamine D2 receptors and serotonin transporters using positron emission tomography in healthy volunteers," Psychopharmacology, vol. 232, pp. 2863-2872, (2015); DOI: 10.1007/s00213-015-3922-1.

Davis, et al., "ITI-007 in the Treatment of Schizophrenia: From Novel Pharmacology to Clinical Outcomes," Expert Review of Neurotherapeutics, vol. 16, No. 6, pp. 601-614, (2016).

Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4): 372 (2017) (Clinical Trials in Alzheimer's Disease (CTAD) Congress, Symposium Summary P93.

Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).

Dhawan et al., "Sleep-related Problems of Parkinson's Disease," *Age and Ageing*, vol. 35, pp. 220-228, (2006); DOI: 10.1093/ageing/afj087.

Dyck, et al., "Effects of Deuterium Substitution on the Catabolism of β-Phenylethylamine: An In Vivo Study," Journal of Neurochemistry, vol. 46, Issue 2, pp. 399-404, (1986).

Fawcett, J., "Posttraumatic Stress Disorder, Stress, and Happiness", Psychiatric Annals Journal, vol. 28, No. 8, pp. 427-428, (1998).

Fletcher et al., "Perceiving is Believing: A Bayesian Approach to Explaining the Positive Symptoms of Schizophrenia," *Nature Reviews/Neuroscience*, vol. 10, pp. 48-58, (2009).

Foster, A.B., "Deuterium Isotope Effects in the Metabolism of Drugs and Xenobiotics: Implications for Drug Design," Advances in Drug Research, vol. 14, pp. 1-40, (1985).

Foster, et al., "Acetylcholinesterase Inhibitors Reduce Spreading Activation in Dementia," Neuropsychologia, vol. 50, pp. 2093-2099, (2012).

Friedman, M.J.., "Current and Future Drug Treatment for Post-traumatic Stress Disorder Patients", Psychiatric Annals Journal, vol. 28, No. 8, pp. 464-468, (1998).

Grant, "Polymorphism in Pharmaceutical Solids", Chapter 1, pp. 1-10 (1999).

Guillory, "Polymorphism in Pharmaceutical Solids", Chapter 5, pp. 183-226 (1999).

(56) References Cited

OTHER PUBLICATIONS

Hackam, et al., "Translation of Research Evidence from Animals to Humans," JAMA, vol. 296, No. 14, pp. 1731-1732, (2006).
Harvey, et al., "Serotonin and Stress: Protective or Malevolent Actions in the Biobehavioral Response to Repeated Trauma?," Annals of the New York Academy of Sciences, vol. 1032, pp. 267-272, (2004); DOI: 10.1196/annals.1314.035.
Haskins, N.J., "The Application of Stable Isotopes in Biomedical Research," Biological Mass Spectrometry, vol. 9, No. 7, pp. 269-277, (1982).
Honma, S., et al., "The Metabolism of Roxatidine Acetate Hydrochloride: Liberation of Deuterium from the Piperidine Ring during Hydroxylation," Drug Metabolism and Disposition, vol. 15, No. 4, pp. 551, (1987).
International Search Report issued in International Application No. PCT/US2019/049061, dated Nov. 13, 2019, 3 pages.
International Search Report issued in International Application No. PCT/US2019/049062, dated Nov. 15, 2019, 3 pages.
Izrayelit, L., "Schizoaffective Disorder and PTSD Successfully Treated With Olanzapine and Supportive Psychotherapy", Psychiatric Annals Journal, vol. 28, No. 8, pp. 424-426, (1998).
Jordan, V.C. Nature Reviews: Drug Discovery, 2, 2003, 205.
Kahn et al., "Residual Symptoms of Schizophrenia. What are Realistic Treatment Goals? Lingering Symptoms Require you to Evaluate Pharmacotherapy and Offer Psychosocial Interventions," *Current Psychiatry*, vol. 16, No. 3, pp. 35-40, (2017).
Kay, et al., "The Positive and Negative Syndrome Scale (PANSS) for Schizophrenia," Schizophrenia Bulletin, vol. 13, No. 2, pp. 261-276, (1987).
Kessler, et al., "Lifetime Prevalence and Age-of-Onset Distributions of DSM-IV Disorders in the National Comorbidity Survey Replication," Arch Gen Psychiatry, vol. 62, pp. 593-602, (2005).
Khorana, et al., "Gamma-Carbolines: Binding at 5-HT5A Serotonin Receptors," Bioorganic & Medicinal Chemistry, vol. 11, pp. 717-722, p. 718 Table 1, (2003).
Koppel, et al., "Optimal Treatment of Alzheimer's Disease Psychosis: Challenges and Solutions," Neuropsychiatric Disease and Treatment, vol. 10, pp. 2253-2262, (2014).
Krystal, J.H., et al., "Adjunctive Risperidone Treatment for Antidepressant-Resistant Symptoms of Chronic Military Service-Related PTSD: A Randomized Trial," JAMA, 306(5):493-502, (2011).
Lammers, L. et al., "Risperidone long-acting injection in Schizophrenia Spectrum Illnesses compared to first generation depot antipsychotics in an outpatient setting in Canada," BMC Psychiatry, 13:155; pp. 1-9 (2013).
Lebert, et al., "Trazodone in Fronto-Temporal Dementia," Research and Practice in Alzheimer's Disease, vol. 11, pp. 356-360, (2006).
Lee, et al. "Novel, Highly Potent, Selective 5-HT2A/D2 Receptor Antagonists as Potential Atypical Antipsychotics," Bioorg. Med. Chem. Lett., vol. 13, pp. 767-770, (2003).
Li et al., "Discovery of a Tetracyclic Quinoxaline Derivative as a Potent and Orally Active Multifunctional Drug Candidate for the Treatment of Neuropsychiatric and Neurological Disorders", vol. 57, pp. 2670-2682 (2014).
Lieberman, et al., "ITI-007 for the Treatment of Schizophrenia: A 4-Week Randomized, Double-Blind, Controlled Trial," Biol. Psychiatry, vol. 79, No. 12, pp. 952-961, (2015).
Lin, et al., "Dosage and Duration of Antipsychotic Treatment in Demented Outpatients with Agitation or Psychosis," Journal of the Formosan Medical Association, vol. 114, pp. 147-153, (2015).
Lipschitz, et al., "Childhood Posttraumatic Stress Disorder: A Review of Neurobiologic Sequelae," Psychiatric Annals Journal, vol. 28, No. 8, pp. 452-457, (1998).
Liriano et al., "Ketamine as treatment for post-traumatic stress disorder: a review." Drugs in Context, vol. 8, 7 pages (2019).
Lopez, et al., "Psychiatric Symptoms Vary with the Severity of Dementia in Probably Alzheimer's Disease," J. Neuropsychiatry Clin. Neurosc., vol. 15, No. 3, pp. 346-353, (2003).

Madhusoodanan, et al., "Pharmacological Management of Behavioral Symptoms Associated with Dementia," World J. Psychiatr., vol. 4, No. 4, pp. 72-79, (2014).
Makadia et al., "Poly Lactic-co-Glycolic Acid (PLGA) as Biodegradable Controlled Drug Delivery Carrier," *Polymers (Basel)*, vol. 3, No. 3, pp. 1377-1397, (2011).
Marek et al. Synergistic Action of 5-HT2A Antagonists and Selective Serotonin Reuptake Inhibitors in Neuropsychiatric Disorders. Neuropsychopharmacology, 2003. Vol. 28, pp. 402-412. (Year: 2003).
Medisorb Fact Sheet, Medisorb Microspheres Technology (retrieved from the internet Nov. 13, 2018), 2 pages (2009).
Mohamed, et al., "Pharmacotherapy of PTSD in the U.S. Department of Veterans Affairs: Diagnostic- and Symptom-guided Drug Selection," J. Clin. Psychiatry, vol. 69, pp. 959-965, (2008).
Morgan, et al., "Acoustic Startle in Individuals With Posttraumatic Stress Disorder," Psychiatric Annals Journal, vol. 28, Issue 8, pp. 430-434, (1998).
Müller et al., "Detection of Depression in Acute Schizophrenia: Sensitivity and Specificity of 2 Standard Observer Rating Scales," *Can J Psychiatry*, vol. 51, No. 6, pp. 387-392, (2006).
Newman et al., "Solid-state analysis of the active pharmaceutical ingredient in drug products", Drug Discovery Today, vol. 8, No. 9, 898-903 (2003).
O'Gorman, et al., "Lumateperone (ITI-007): A Novel Investigational Agent with Broad Therapeutic Potential Across Multiple Neuropsychiatric Disorders," Poster P.1.g.038, European College of Neuropsychopharmacology (ECNP) Congress (2017).
Palanisamy, M. et al., "Cellulose-Based Matrix Microspheres of Prednisolone Inclusion Complex; Preparation and Characterization." American Association of Pharmaceutical Scientists PharmSciTech, vol. 12, No. 1, pp. 388-400, (2011).
Perlis et al., "Clinical Features of Bipolar Depression Versus Major Depressive Disorder in Large Multicenter Trials", *Am J Psychiatry*, vol. 163, vol. 2, p. 225-231, (2006).
Pieniaszek, et al., "Moricizine Bioavailability via Simultaneous Dual, Stable Isotope Administration: Bioequivalence Implications," J. Clin. Pharmacol., vol. 39, pp. 817-825, (1999).
Pine et al., "Dopamine, Time, and Impulsivity in Humans," *The Journal of Neuroscience*, vol. 30, No. 26, pp. 8888-8896, (2010).
Press Release, "Intra-Cellular Therapies Announces Additional Results from Phase I/II Clinical Trial for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=884325), accessed on May 31, 2016.
Pubchem, OPEN Chemistry Database, PubChem SID 103920954, PubChem CID 90655118, (2011), 6 pages.
Rackova, et al., "Free Radical Scavenging and Antioxidant Activities of Substituted Hexahydropyridoindoles. Quantitative Structure-Activity Relationships." Journal of Medicinal Chemistry, vol. 49, No. 8, pp. 2543-2548, (2006).
Rainer, M.K., "Risperidone Long-acting Injection: A Review of its Long Term Safety and Efficacy," Neuropsychiatric Disease and Treatment, vol. 4, No. 5, pp. 919-927, (2008).
Ramaswamy et al., "Failed Efficacy of Ziprasidone in the Treatment of Post-Traumatic Stress Disorder," *Contemporary Clinical Trials Communications*, vol. 2, pp. 1-5, (2016).
Reynolds et al., "Longitudinal Change in Memory Performance Associated with HTR2A Polymorphism," *Neurobiology of Aging*, vol. 27, pp. 150-154, (2006).
Rye (Sleep Disorders and Parkinson's Disease, 2000, accessed online http://www.waparkinsons.org/edu_research/articles/Sleep_Disorders.html), 2 pages.
Satlin, et al., "ITI-007 (Lumateperone) for the Treatment of Agitation in Patients with Dementia, including Alzheimer's Disease," Alzheimer's & Dementia 14(7) (Suppl.): P678-79 (2018) (Alzheimer's Assoc. International Conference 2018, summary of Poster P2-032).
Satlin, et al., "ITI-007 (Lumateperone) for the Treatment of Agitation in Patients with Dementia, including Alzheimer's Disease," Poster P2-032, Alzheimer's Assoc. International Conference 2018 (2018).

(56) References Cited

OTHER PUBLICATIONS

Savjani et al., "Drug Solubility: Importance and Enhancement Techniques", International Scholarly Research Network Pharmaceutics (2012), vol. 2012, pp. 1-10.
Schennach et al., "What Are Residual Symptoms in Schizophrenia Spectrum Disorder? Clinical Description and 1-year Persistence Within a Naturalistic Trial," *Eur. Arch. Psychiatry Clin. Neurosci.*, vol. 265, pp. 107-116, (2015); DOI: 10.1007/s00406-014-0528-2.
Seishinkei Shi, vol. 110, No. 7, pp. 557-584, (2008). Partial English translation only.
Semla et al., "Off-Label Prescribing of Second-Generation Antipsychotics to Elderly Veterans with Posttraumatic Stress Disorder and Dementia," *J. Am. Geriatr. Soc.*, vol. 65, No. 8, pp. 1789-1795, (2017); DOI: 10.1111/jgs.14897.
Singhal, et al., "Drug Polymorphism and Dosage Form Design: A Practical Perspective," Advanced Drug Delivery Reviews, vol. 56, pp. 335-347, (2004).
Snyder et al., "Functional profile of a novel modulator of serotonin, dopamine, and glutamate neurotransmission", Psychopharmacology, 232:605-621 (2015).
Southwick, et al., "Neuroendocrine Alterations in Posttraumatic Stress Disorder," Psychiatric Annals Journal, vol. 28, No. 8, pp. 436-442, (1998).
Taragano, et al., "A Double-Blind, Randomized, Fixed-Dose Trial of Fluoxetine vs. Amitriptyline in the Treatment of Major Depression Complicating Alzheimer's Disease," Psychosomatics, vol. 38, No. 3, pp. 246-252, (1997).
Timmins, G.S., "Deuterated drugs: where are we now?" Expert Opinion on Therapeutic Patents, 1-9 (2014).
Tung, R., "The Development of Deuterium-Containing Drugs," Innovations in Pharmaceutical Technology, vol. 32, pp. 1-4, (2010).
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.
Vanover, et al., "Dopamine D2 receptor occupancy of lumateperone (ITI-007): a Positron Emission Tomography Study in patients with schizophrenia," Neuropsychopharmacology 44:598-605, (2019).
Vanover, K., et al., "ITI-007: A Novel Therapy for the Treatment of Schizophrenia and Related Psychoses," International Clinical Psychopharamcology, vol. 26, e56, 1 page, (2011).
Vloeberghs et al., "Altered Circadian Locomotor Activity in APP23 Mice: A Model for BPSD Disturbances," *European Journal of Neuroscience*, vol. 20, pp. 2757-2766, (2004); DOI: 10.1111/j.1460-9568.2004.03755.x.
Vyas et al., "An Evaluation of Lumateperone Tosylate for the Treatment of Schizophrenia," *Expert Opinion on Pharmacotherapy*, vol. 21, No. 2, pp. 139-145, (2020); https://doi.org/10.1080/14656566.2019.1695778.
Warner-Schmidt JL. et al. "Antidepressant effects of selective serotonin reuptake inhibitors (SSRis) are attenuated by anti-inflammatory drugs in mice and humans". Proc.Natl. Acad.Sci., 108(22):9262-7 (2011).
Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.
Weschules, et al., "Acetylcholinesterase Inhibitor and N-Methyl-D-Aspartic Acid Receptor Antagonist Use among Hospice Enrollees with a Primary Diagnosis of Dementia," Journal of Palliative Medicine, vol. 11, No. 5, pp. 738-745, (2008).
Wiese, M., "DSC Detection of Polymorphism in Pharmaceutical Anhydrous Dexamethasone Acetate," TA Instruments, TA 302, pp. 1-4, (2002).
Wolen, R. L., "The Application of Stable Isotopes to Studies of Drug Bioavailability and Bioequivalence," J. Clin. Pharmacol., vol. 26, pp. 419-424, (1986).
Zhang et al., "The Role of Serotonin 5-HT2A Receptors in Memory and Cognition," *Front. Pharmacol.*, vol. 6, No. 225, pp. 1-17, (2015); DOI: 10.3389/fphar.2015.00225.

\* cited by examiner

METHODS

CROSS-REFERENCE TO RELATED APPLICATIONS

This application is a U.S. National Stage application under 35 U.S.C. § 371 of International Application No. PCT/US2019/049061, filed on Aug. 30, 2019, which claims priority to and, the benefit of, U.S. Provisional Application No. 62/725,944, filed on Aug. 31, 2018, and U.S. Provisional Application No. 62/779,920, filed on Dec. 14, 2018, the contents of each of which are hereby incorporated by reference in their entireties.

TECHNICAL FIELD

The present disclosure relates to solid oral dosage forms comprising lumateperone, in free, or pharmaceutically acceptable salt form, optionally in combination with one or more additional therapeutic agents, processes for manufacture thereof and methods of use in the treatment or prophylaxis of disease.

BACKGROUND OF THE INVENTION

The substituted heterocycle fused gamma-carbolines lumateperone (4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone) is known to be a serotonin receptor (5-HT2A), dopamine receptor (D1 and/or D2), and serotonin transporter (SERT) ligand, which is useful in treating a variety of central nervous system disorders.

Lumateperone antagonizes the serotonin-2A (5-HT2A) receptor, and/or modulates dopamine receptor signaling at the level of key intra-cellular phosphoproteins. This compound is principally known to be useful for the treatment of positive and negative symptoms of schizophrenia, depression (especially acute depression and bipolar depression), anxiety and traumatic disorders (including acute anxiety and post-traumatic stress disorder), and dementias (including Alzheimer's disease and the symptoms associated therewith). At dopamine D2 receptors, this compound has dual properties and acts as both a post-synaptic antagonist and a pre-synaptic partial agonist of the D2 receptor. It also stimulates phosphorylation of glutamatergic NMDA NR2B, or GluN2B, receptors in a mesolimbic specific manner. It is believed that this regional selectivity in the brain areas thought to mediate the efficacy of antipsychotic drugs, together with the serotonergic, glutamatergic, and dopaminergic interactions, may result in antipsychotic efficacy for positive, negative, affective and cognitive symptoms associated with schizophrenia. The compound also exhibits serotonin reuptake inhibition, providing antidepressant activity for the treatment of schizoaffective disorder, co-morbid depression, and/or as a stand-alone treatment for major depressive disorder. Lumateperone is also useful for the treatment of bipolar disorder and other psychiatric and neurodegenerative disorders, particularly behavioral disturbances associated with dementia, autism and other CNS diseases. These features may be able to improve the quality of life of patients with schizophrenia and enhance social function to allow them to more fully integrate into their families and their workplace. Lumateperone displays differential dose-dependent effects, selectively targeting the 5-HT2A receptor at low doses, while progressively interacting with the D2 receptor at higher doses. As a result, at lower doses, it is useful in treating sleep, aggression and agitation. At a high dose, it can treat acute exacerbated and residual schizophrenia, bipolar disorders, and mood disorders.

Lumateperone, having the formula:

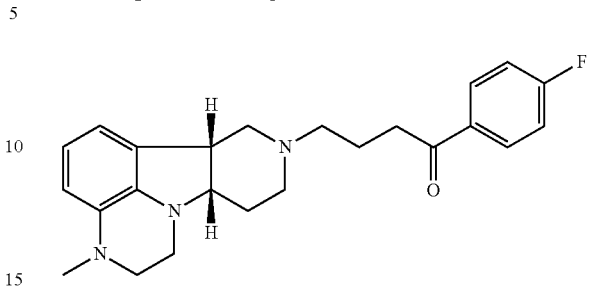

is a novel therapeutic agent with potent (Ki=0.5 nM) 5-HT$_{2A}$ receptor antagonism, activity as a mesolimbic/mesocortical-selective dopamine receptor protein phosphorylation modulator consistent with presynaptic D2 receptor partial agonism and postsynaptic D2 receptor antagonism (Ki=32 nM) in vivo, high D1 receptor affinity (Ki=52 nM), and inhibition of the serotonin transporter (SERT) (Ki=26-62 nM, using different assays for SERT activity). Lumateperone is in Phase III clinical development as a treatment for schizophrenia, bipolar depression and agitation in dementia, including Alzheimer's Disease.

Lumateperone and related compounds have been disclosed in U.S. Pat. Nos. 6,548,493, 7,238,690, 6,552,017, 6,713,471, U.S. RE39680, and U.S. RE39679 (each of which are incorporated herein by reference) as novel compounds useful for the treatment of disorders associated with 5-HT2A receptor modulation such as anxiety, depression, psychosis, schizophrenia, sleep disorders, sexual disorders, migraine, conditions associated with cephalic pain, and social phobias. PCT/US08/03340 and U.S. Pat. No. 7,081,455, incorporated by reference herein, also disclose methods of making substituted heterocycle fused gamma-carbolines and uses of these gamma-carbolines as serotonin agonists and antagonists useful for the control and prevention of central nervous system disorders such as addictive behavior and sleep disorders. WO 2009/145900 and U.S. Pat. No. 8,598,119, and WO 2013/155506 and US 2015/0080404, each incorporated herein by reference, disclose the use of specific substituted heterocycle fused gamma-carbolines for the treatment of a combination of psychosis and depressive disorders as well as sleep, depressive and/or mood disorders in patients with psychosis or Parkinson's disease and for the treatment or prophylaxis of disorders associated with dementia, particularly behavioral or mood disturbances such as agitation, irritation, aggressive/assaultive behavior, anger, physical or emotional outbursts and psychosis and sleep disorders associated with dementia. WO 2009/114181 and U.S. Pat. No. 8,648,077, each incorporated herein by reference, disclose methods of preparing toluenesulfonic acid addition salt crystals of particular substituted heterocycle fused gamma-carbolines, e.g., toluenesulfonic acid addition salt of 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone.

WO 2011/133224 and U.S. Pat. No. 8,993,572, each incorporated herein by reference, disclose prodrugs/metabolites of substituted heterocycle fused gamma-carboline for improved formulation, e.g., extended/controlled release formulation. This application discloses that heterocycle fused gamma-carboline N-substituted with a 4-fluorophenyl(4-hydroxy)butyl moiety are shown to have high selectivity for the serotonin transporter (SERT) relative to the heterocycle fused gamma-carboline containing 4-fluorophenylbutanone.

WO 2009/145900 (and U.S. Pat. No. 8,598,119, incorporated herein by reference) teaches that selected substituted heterocycle fused gamma-carboline compounds have nanomolar affinity for the serotonin reuptake transporter (SERT) and so are selective serotonin reuptake inhibitors.

It has also recently been found that lumateperone may be particularly effective in treating acute depression and acute anxiety owing to its rapid onset of action compared to existing antidepressants, as disclosed in PCT/US2019/035845 (incorporated herein by reference in its entirety). This is believed to be due to its signaling through a neurotransmitter system separate from the traditional monoamine signaling systems. Lumateperone provides a dopamine D1 receptor-dependent enhancement of NMDA and AMPA currents coupled with activation of the mTOR (e.g., mTORC1) signaling pathway.

BRIEF SUMMARY OF THE INVENTION

The present disclosure provides solid oral dosage forms comprising lumateperone in free or pharmaceutically acceptable salt form. In some embodiments, the dosage form is a tablet. In some embodiments the dosage form further comprises one or more additional therapeutic agents. These dosage forms are useful for the treatment or prophylaxis of a variety of central nervous system disorders.

DETAILED DESCRIPTION

Lumateperone is a novel therapeutic agent with potent (Ki=0.5 nM) 5-HT2A receptor antagonism, activity as a mesolimbic/mesocortical-selective dopamine receptor protein phosphorylation modulator consistent with presynaptic D2 receptor partial agonism and postsynaptic D2 receptor antagonism (Ki=32 nM) in vivo, high D1 receptor affinity (Ki=52 nM), and inhibition of the serotonin transporter (SERT) (Ki=26-62 nM, using different assays for SERT activity). Lumateperone is in Phase III clinical development as a treatment for schizophrenia, bipolar depression and agitation in dementia, including Alzheimer's Disease.

The present disclosure provides a solid oral dosage form (Dosage Form 1), comprising lumateperone:

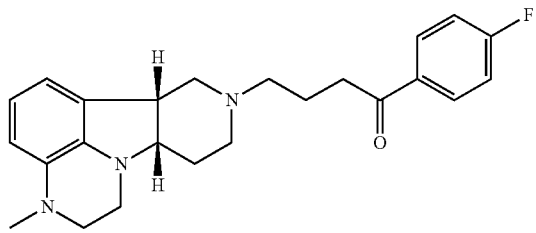 [SMILES: CN1CCN2c3c(cccc31)[C@@H]1CN(CCCC(=O)c3ccc(F)cc3)CC[C@@H]12]

in free or pharmaceutically acceptable salt form (e.g., in tosylate salt form), optionally wherein the dosage form is an immediate release dosage form. For example, Dosage Form 1 may be as follows:
1.1. Dosage Form 1, wherein the dosage form comprises lumateperone in free base form (e.g., in free base solid amorphous dispersion form);
1.2. Dosage Form 1, wherein the dosage form comprises lumateperone in pharmaceutically acceptable salt or co-crystal form;
1.3. Dosage Form 1, wherein the dosage form comprises lumateperone in tosylate salt form, e.g., in one or more of mono-tosylate salt form, di-tosylate salt form, and tri-tosylate salt form;
1.4. Dosage Form 1.3, wherein the dosage form comprises a combination of lumateperone in mono-tosylate salt form and lumateperone in di-tosylate salt form;
1.5. Any of Dosage Forms 1 or 1.1-1.3, wherein the Dosage Form comprises lumateperone in mono-tosylate salt form;
1.6. Dosage Form 1.5, wherein the lumateperone mono-tosylate is in solid crystal form, e.g., having the physical and chemical properties as disclosed in U.S. Pat. No. 8,648,077, such as one or more of the XRPD spectrum, IR spectrum, and/or DSC/TGA spectrum as disclosed therein;
1.7. Dosage Form 1.5, wherein the lumateperone mono-tosylate is in solid crystal form, wherein the crystal exhibits an X-ray powder diffraction pattern comprising at least two peaks having 2-theta values selected from the group consisting of 5.68°, 12.11°, 16.04°, 17.03°, 18.16°, 19.00°, 21.67°, 22.55°, 23.48° and 24.30°, each of said peaks ±0.2°, e.g., wherein the X-ray powder diffraction data is collected on a diffractometer operating with a copper anode with a nickel filter;
1.8. Dosage Form 1.5, wherein the lumateperone mono-tosylate is in solid crystal form, wherein the crystal exhibits an X-ray powder diffraction pattern comprising at least five peaks having 2-theta values selected from the group consisting of: 5.68°, 12.11°, 16.04°, 17.03°, 18.16°, 19.00°, 21.67°, 22.55°, 23.48° and 24.30°, each of said peaks ±0.2°, e.g., wherein the X-ray powder diffraction data is collected on a diffractometer operating with a copper anode with a nickel filter;
1.9. Dosage Form 1.5, wherein the lumateperone mono-tosylate is in solid crystal form, wherein the crystal exhibits an X-ray powder diffraction pattern comprising the following peaks having 2-theta values: 5.6811°, 8.5140°, 11.3750°, 12.1088°, 13.3354°, 15.7948°, 16.0419°, 16.4461°, 17.0309°, 17.2606°, 17.5531°, 18.1581°, 18.9968°, 19.8889°, 20.7510°, 21.6724°, 22.25463°, 23.4815°, 23.7411°, 24.3006°, 25.9394°, 27.2321°, 28.3782°, 28.9055°, 29.6695°, 31.6106°, 32.2950°, 34.8530°, 37.5435°, 39.4972°, 40.2502° and 40.8303°, each of said peaks ±0.2°, e.g., wherein the X-ray powder diffraction data is collected on a diffractometer operating with a copper anode with a nickel filter;
1.10. Any of Dosage Forms 1.3-1.5, wherein the lumateperone tosylate, e.g., the lumateperone mono-tosylate, is in solid amorphous form or is in the form of a solid amorphous dispersion.
1.11. Dosage Form 1.10, wherein the lumateperone tosylate, e.g., the lumateperone mono-tosylate, is in the form of a solid amorphous dispersion comprising amorphous lumateperone tosylate in admixture with one or more excipients, e.g., stabilizing excipients.
1.12. Dosage Form 1.11, wherein the dosage form comprises one or more excipients which stabilize the amorphous from of ITI-007 tosylate to prevent conversion of the amorphous form to the crystal form.
1.13. Dosage Form 1.11 or 1.12, wherein the one or more excipients are selected from the group consisting of cellulose acetate, cellulose acetate phthalate, methacrylate/methyl acrylate copolymer, hydroxypropyl cellulose, hydroxypropyl methyl cellulose, hydroxypropyl methyl cellulose acetate succinate (HPMC-AS), hydroxypropyl methyl cellulose phthalate (HPMC-P), polyvinyl acetate, polyvinyl pyrrolidone, polyvinyl pyrrolidone/vinyl acetate copolymer, and polyethylene glycol/polyvinyl acetate/polyvinylcaprolactam copolymer.

1.14. Any of Dosage Forms 1.11-1.13, wherein the dosage form further comprises an anti-oxidant, e.g., selected from one or more of tocopherol, butylated hydroxytoluene (BHT), propyl gallate (OPG), ascorbic acid, butylated hydroxyanisole (BHA), tert-Butylhydroquinone (TBHQ), carotenoids, glutathione, sodium metabisulfite, sodium ethylenediaminetetraacetate, cysteine, methionine, sesamol, and citric acid.

1.15. Any of Dosage Forms 1.11-1.14, wherein the dosage form further comprises a surfactant, e.g., an anionic, cationic, zwitterionic or neutral surfactant.

1.16. Any of Dosage Forms 1.5-1.15, wherein the Dosage Form further comprises toluenesulfonic acid, e.g., in a molar ratio of about 1:1 to 1:2 with respect to the lumateperone mono-tosylate, e.g., 1:1 to 1:1.5 molar ratio, or 1:1 to 1:2 molar ratio, or about a 1:1 molar ratio;

1.17. Dosage Form 1 or any of 1.1-1.16, wherein the Dosage Form comprises the lumateperone, in free and/or pharmaceutically acceptable salt form in a total unit amount equivalent to 0.01 to 120 mg of lumateperone free base, e.g., 0.01 to 100 mg, 0.01 to 75 mg, 0.01 to 50 mg, 0.01 to 30 mg, 0.01 to 20 mg, 0.1 to 20 mg, 5 to 20 mg, 10 to 20 mg, 10 to 30 mg, 20 to 30 mg, 20 to 50 mg, 30 mg to 50 mg, 50 to 100 mg, 1 to 75 mg, or 1 to 60 mg, or 1 to 40 mg, or 1 to 20 mg, 1 to 10 mg, 25 to 35 mg, or 35 to 45 mg, or about 6 mg, about 14 mg, or about 28 mg, or about 42 mg;

1.18. Dosage Form 1 or any of 1.1-1.17, further comprising one or more pharmaceutically acceptable diluents or carriers (i.e., excipients);

1.19. Dosage Form 1.18, wherein the one or more pharmaceutically acceptable diluents or carriers comprises one or more of (a) diluent/filler (e.g., cellulose or microcrystalline cellulose (e.g., silicified microcrystalline cellulose), mannitol, lactose monohydrate, dicalcium phosphate, or isomalt), (b) binder (e.g., hydroxypropyl cellulose, hydroxypropyl methyl cellulose, copovidone), (c) disintegrant (e.g., sodium starch glycolate, crospovidone or croscarmellose sodium), (d) lubricant (e.g., magnesium stearate or glyceryl monostearate), (e) glidant (e.g., silicon dioxide or talc), (f) effervescent, (g) polymer, (h) plasticizer, (i) drying agent or desiccant, (j) humectant (e.g., polyol), (k) wetting agent, (1) anti-oxidant (e.g., BHT, citric acid, propyl gallate, ascorbic acid or sodium metabisulfite), (m) thickening agent (e.g., gelling agent), (n) surfactant, (o) buffer, (p) sweetener or flavor, and (q) dye or colorant;

1.20. Dosage Form 1.18, wherein the one or more pharmaceutically acceptable diluents or carriers comprises one or more hydrophilic water-soluble or water swellable polymers;

1.21. Dosage Form 1.20, wherein the polymer is selected from the group consisting of natural or modified cellulosic polymers, polymers of ethylene oxide and/or propylene oxide, polymers comprising acrylic acid monomers, natural or modified gums (e.g. xanthan gum), natural or modified starches (e.g., pre-gelatinized starches), or any mixture thereof;

1.22. Dosage Form 1.20, wherein the one or more pharmaceutically acceptable diluents or carriers comprises one or more hydrophobic polymers or poorly water-soluble polymers, for example, a silicone polymer, or polyalkylene polymer (e.g., polyethylene);

1.23. Dosage Form 1.20, wherein the one or more pharmaceutically acceptable diluents or carriers comprises are selected from any of the following: alcohols (ethanol, glycerol, propylene glycol), gums (e.g., acacia, guar, agar, xanthan, tragacanth, karaya, gellan), polysaccharides and polysaccharide derivatives (e.g., starches, dextrans, pectins, alginates, carrageenans, cellulose, cellulose derivatives (e.g., carboxymethyl cellulose, methylcellulose, hydroxyalkyl celluloses (e.g., hydroxyethyl cellulose, hydroxypropyl cellulose, hydroxypropyl methyl cellulose)), gelatins including non-gelling and gelling types (e.g., mammalian gelatins such as bovine gelatin, porcine gelatins, avian gelatins, fish gelatins (e.g., mixed high molecular weight and low molecular weight gelatins), synthetic polymers (e.g., polyvinylpyrrolidones, polyethylene oxide and/or polypropylene oxide polymers and copolymers (e.g., poloxamers, such as poloxamer 188), polyacrylate polymers (e.g., carbopols), polyamide polymers, sugars and sugar alcohols (e.g., dextrose, lactose, galactose, glucose, ribose, sucrose, trehalose, mannitol, maltitol, lactitol, sorbitol, xylitol, erythritol, galactitol, inositol), polypeptides/proteins, amino acids, inorganic or organic acids (e.g., citric acid, lactic acid, malic acid, gluconic acid, benzoic acid, toluenesulfonic acid, phosphoric acid, sulfuric acid, hydrochloric acid, tartaric acid, oxalic acid, cyclamic acid, ascorbic acid, methanesulfonic acid, benzenesulfonic acid, formic acid) and their salts (e.g., sodium, potassium, calcium, magnesium, lithium, ammonium salts of aforementioned acids), inorganic or organic bases (e.g., alkali metal or alkaline earth metal carbonates, bicarbonates, hydroxide, oxides), anionic surfactants (e.g., sodium lauryl sulfate, sodium laureth sulfate, sodium dodecylbenzenesulfonate, sodium lauroyl sarcosinate, sodium stearate), cationic surfactants (e.g., benzalkonium halides, cetylpyridinium halides, cetrimonium halides, benzethonium halides), zwitterionic surfactants (e.g., cocamidoalkyl betaines, such as cocamidopropyl betaine), nonionic surfactants (e.g., fatty alcohol ethoxylates (e.g., polyethylene glycol polydodecyl ethers)), sorbitan esters (e.g., sorbitan monolaurate, sorbitan monooleate, sorbitan monopalmitate, sorbitan monostearate, sorbitan tristearate), polyethoxylated sorbitan esters (e.g., polysorbate 20, polysorbate 40, polysorbate 60, polysorbate 80), and antioxidants (e.g., ascorbic acid, citric acid, ascorbyl palmitate, sodium metabisulfite, sodium sulfite, BHT, BHA, TBHQ, propyl gallate, beta-carotene, tocopherols, tocotrienols, citric acid, EDTA);

1.24. Dosage Form 1 or any of 1.1-1.23, wherein the dosage form comprises or consists of (a) lumateperone tosylate (e.g., mono-tosylate), lactose monohydrate, starch (e.g., pregelatinized starch), cellulose (e.g., microcrystalline cellulose, optionally silicified), hydroxypropyl cellulose (HPC), hydroxypropyl methyl cellulose (HPMC), copovidone (cross-linked polyvinyl pyrrolidone), sodium starch glycolate, flavors and/or colors and/or antioxidants, or (b) lumateperone tosylate (e.g., mono-tosylate), cellulose (e.g., microcrystalline cellulose, optionally silicified), hydroxypropyl cellulose (HPC), croscarmellose sodium (cross-linked carboxymethyl cellulose sodium); silicon dioxide (e.g., colloidal silicon dioxide), magnesium stearate, flavor and/or colors and/or antioxidants;

1.25. Any of Dosage Forms 1.12-1.24, wherein any one or more of each said pharmaceutically acceptable carriers or diluents are present in an amount of 0.01 to 80% by weight of the Dosage Form, e.g., 0.1 to 60%, or 0.1 to 40%, or 0.1 to 30%, 0.01 to 15%, or 0.01 to 10%, or 0.1 to 20%, or 0.1 to 15% or 0.1 to 10%, or 0.5 to 10%, or 0.5 to 5%, or 1 to 5%, or 2.5 to 5%, or 1 to 3%, or 0.1 to 1%; optionally wherein the Dosage Form comprises from 60 to 90% by weight of diluent/filler, e.g., 70 to 80% diluent/filler;

1.26. Any of Dosage Forms 1.12-1.25, wherein the Dosage Form comprises from 1% to 90% lumateperone, in free and/or in pharmaceutically acceptable salt form (e.g. tosylate), by weight of the composition and measured as the total content of lumateperone in all forms thereof, e.g., 1% to 80%, or 1% to 70%, or 1% to 60%, or 1% to 50%, or 1% to 40%, or 1% to 30%, or 1% to 20% or 1% to 15%, or 1% to 10%, or 1% to 5%, or 5% to 10%, or 10% to 20%, or 20 to 30%, lumateperone, in free and/or pharmaceutically acceptable salt form;

1.27. Any preceding Dosage Form, wherein the Dosage Form comprises about 60 to 90% by weight of diluents/ fillers (e.g., cellulose or microcrystalline cellulose (e.g., silicified microcrystalline cellulose), mannitol, lactose monohydrate, dicalcium phosphate, or isomalt), and about 1 to 10% by weight of binders (e.g., hydroxypropyl cellulose, hydroxypropyl methyl cellulose, copovidone), and about 1 to 10% by weight of disintegrants (e.g., sodium starch glycolate, crospovidone or croscarmellose sodium), and about 0.1 to 5% by weight of lubricants (e.g., magnesium stearate or glyceryl monostearate), and about 0.1 to 5% by weight of glidants (e.g., silicon dioxide or talc), and about 0.1 to 5% by weight of anti-oxidants (e.g., BHT, citric acid, propyl gallate, ascorbic acid or sodium metabisulfite);

1.28. Any preceding Dosage Form, wherein the dosage form comprises one or more surface coatings, e.g., polymer surface coatings (e.g., comprising polyvinyl alcohol), optionally wherein the Dosage Form comprises 1-10% by weight of the polymer surface coating(s);

1.29. Any preceding Dosage Form wherein the Dosage Form is a tablet, e.g., a spherical (e.g., round) or approximately spherical (e.g., oval or oblong) tablet;

1.30. Any preceding Dosage Form wherein the Dosage Form is a caplet, e.g., a capsule-shaped tablet;

1.31. Any preceding Dosage Form wherein the lumateperone is present in (a) a mean particle size of 1 to 200 µm, e.g., 1 to 150 µm, 1 to 100 µm, 1 to 50 µm, 1 to 25 µm, 1 to 15 µm, 1 to 10 µm, 5 to 10 µm, or 1 to 5 µm; and/or (b) a D90 of 100 µm or less, 50 µm or less, 25 µm or less, 15 µm or less, or 10 µm or less; and/or (c) a D10 of 50 µm or less, 25 µm or less, 15 µm or less, or 10 µm or less, or 5 µm or less;

1.32. Dosage Form 1 or any of 1.1-1.31, wherein the Dosage Form is formulated for oral (gastrointestinal) administration;

1.33. Dosage Form 1 or any of 1.1-1.31, wherein the Dosage Form is formulated for oral transmucosal administration, e.g., for sublingual or buccal oral disintegration;

1.34. Any foregoing Dosage Form wherein the lumateperone is in combination (e.g. a fixed combination) with an effective amount of an additional therapeutic agent;

1.35. Dosage Form 1.34, wherein the additional therapeutic agent is an anxiolytic or antidepressant agent;

1.36. Dosage Form 1.35, wherein the anxiolytic or antidepressant agent is selected from one or more compounds in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g. one or more compounds in free or pharmaceutically acceptable salt form, selected from:
 (a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);
 (b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);
 (c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);
 (d) Benzodiazepines, e.g., selected from 2-keto compounds (e.g., clorazepate, diazepam, flurazepam, halazepam, prazepam); 3-hydroxy compounds (lorazepam, lormetazepam, oxazepam, temazepam); 7-nitro compounds (e.g., clonazepam, flunitrazepam, nimetazepam, nitrazepam); triazolo compounds (e.g., adinazolam, alprazolam, estazolam, triazolam); and imidazo compounds (climazolam, loprazolam, midazolam);

1.37. Dosage Form 1.35, wherein the additional antidepressant agent is selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/ NRI, an SRI/DRI, an NRI/DRI, an SRI/NRI/DRI (triple reuptake inhibitor), a serotonin receptor antagonist, or any combination thereof);

1.38. Dosage Form 1.36, wherein the additional therapeutic agent is a NMDA receptor antagonist, for example, selected from ketamine (e.g., S-ketamine and/or R-ketamine), hydroxynorketamine, memantine, dextromethorphan, dextroallorphan, dextrorphan, amantadine, and agmatine, or any combination thereof;

1.39. Any preceding Dosage Form, wherein the Dosage Form is manufactured by a dry-blending or dry-granulating process;

1.40. Any preceding Dosage Form, wherein the Dosage Form is intended to be administered once daily, or twice daily, or three times daily, or every other day, or every third day;

1.41. Any preceding Dosage Form, wherein the Dosage Form is packaged in a blister pack (e.g., push-through pack), e.g., a blister pack made of any suitable material (e.g., aluminum foil, polyvinyl chloride, polyvinylidene chloride, polychlorotrifluoroethylene, cyclic olefin copolymers, polyethylene, polypropylene, polyethylene terephthalate, or a combination thereof);

1.42. Any preceding dosage form, wherein the Dosage Form is packaged in a bottle (e.g., plastic or glass, optionally with a screw cap lid or a child-proof lid), optionally wherein the bottle has a compartment to hold a desiccant (e.g., silica or calcium chloride);

1.43. Any preceding dosage form, wherein the Dosage Form is formulated for immediate-release;

1.44. Any preceding dosage form, wherein the Dosage Form is formulated for delayed or sustained release.

1.45. Any preceding dosage form, wherein the dosage form does not comprise an antioxidant;

1.46. Any preceding dosage form, wherein the dosage form comprises an antioxidant selected from ascorbic acid and citric acid;

1.47. Any preceding dosage form, wherein the an assay (e.g., by RP HPLC) of the dosage form at or shortly after the time of manufacture demonstrates that the dosage form comprises from 90-110% of the label amount of lumateperone (in free or pharmaceutically acceptable salt form), and/or that the dosage form comprises not more than 0.5% (e.g., as measured by RP-HPLC) of any single related substance impurity and not more than 3.0% (e.g., as measured by RP-HPLC) of all related substance impurities combined;

1.48. Any preceding dosage form, wherein the an assay (e.g., by RP HPLC) of the dosage form at up to three months after manufacture (e.g., 1, 2 or 3 months) after the time of manufacture demonstrates that the dosage form comprises from 90-110% of the label amount of lumateperone (in free or pharmaceutically acceptable salt form), and/or that the dosage form comprises not more than 0.5% (e.g., as measured by RP-HPLC) of any single related substance impurity and not more than 3.0% (e.g., as measured by RP-HPLC) of all related substance impurities combined, for example, when the dosage form is stored for the up the three months period at ambient temperature and humidity or at elevated temperature (e.g., 40-50° C.) and/or at elevated humidity (e.g., 60-75% relative humidity);

1.49. Any preceding dosage form, wherein the dosage form dissolves in 500 mL of 0.1N aqueous hydrochloric acid to the extent of at least 75% after 15 minutes (e.g., 80-90%), and/or to the extent of at least 90% after 30 minutes (e.g., 92-98%), and/or at least 92% after 45 minutes (e.g., 95-99%).

In some embodiments, binders may include one or more of hydroxypropyl cellulose, hydroxypropyl methylcellulose, ethyl cellulose, methylcellulose, polyvinyl pyrrolidone, povidone, polyvinyl alcohol, gum arabic powder, gelatin, pullulan and the like. Each solid dosage form may comprise from 0.5-10% by weight, e.g., 1-5%, or 1-3% by weight each binder.

Carmellose calcium, croscarmellose sodium, sodium starch glycolate, crospovidone, low substituted hydroxypropyl cellulose, powdered agar and the like are used as the disintegrant. The disintegrants such as sodium starch glycolate, croscarmellose sodium and low substituted hydroxypropyl cellulose are preferable. Each tablet can contain 0.1-15% by weight, preferably 1-5% by weight of the disintegrant.

In some embodiments, the solid dosage form of the present disclosure further comprises an appropriate amount of a flavor, a lubricant, a coloring agent and the like, or various additives which are commonly used for preparing a galenic formulation. Lubricants may include magnesium stearate, calcium stearate, sucrose fatty acid ester, polyethylene glycol, talc, stearic acid, sodium stearyl fumarate and the like. Coloring agents may include the food colors such as food yellow no. 5, food red no. 2, food blue no. 2, food lake colors, iron sesquioxide and the like.

In some embodiments, a coating mixture may be applied to the solid dosage form by using a well-known method with the purpose of, for example, further masking of a taste and an odor, and preparation of an enteric formulation or a sustained-release formulation after coating a particle core with the active ingredient, one or more additives and the like. Coating mixtures may comprise any suitable water-soluble or water-swellable polymers, such as polyvinyl alcohol, polyvinyl pyrrolidone, polyethylene glycol, and polyacrylic acid, for example.

The solid dosage forms of the present disclosure include, for example, tablets, caplets, and pills. They do not include capsules or the granules used in capsules. A tablet may have a variety of shapes, including but not limited to, round, oval, square, rectangular, and oblong. Tablets and caplets may optionally be scored for easier cutting. Tablets and caplets may be coated with one, two, three or more layers designed for different purposes (e.g., taste-masking, enteric protection, delayed or sustained release, improve swallowing).

The solid dosage forms of the present disclosure may further include any one or more of pharmaceutically acceptable solvents, surface tension modifiers (e.g., surfactants), preservatives, antioxidants, colorants, taste masking agents, flavors and sweeteners. Examples of solvents include water and other solvents, which are miscible with water or solubilizing agents and suitable for oral purposes. Examples of suitable solvents are ethanol, propylene glycol, glycerol, polyethylene glycols, poloxamers, sorbitol and benzyl alcohol. In some embodiments, the aqueous solubility of the lumateperone may further be enhanced by the addition to the solution of a pharmaceutically acceptable co-solvent, a cyclodextrin or a derivative thereof (e.g., dextrans).

Preservative agents may be added to prevent the growth of microorganisms such as bacteria, yeasts and fungi in liquid formulations, which are likely to be used repeatedly. Suitable preservatives should be physicochemical stable and effective in the desired pH range. Examples of preservative agents include ethanol, methylparaben, propylparaben and benzyl alcohol.

In some embodiments, the solid dosage forms of the present disclosure include one or more anti-oxidants to guard against degradation of the active. Examples of antioxidants include propyl gallate, ascorbyl palmitate, ascorbic acid, t-butylhydroquinone (TBHQ), butylated hydroxyanisole (BHA), butylated hydroxytoluene (BHT), tocopherols, tocotrienols, sodium sulfite, sodium metabisulfite, beta-carotene, citric acid and EDTA.

In some embodiments, coloring agents may be used to introduce a uniformity of appearance to the product and/or to protect any light-sensitive ingredients. Suitable coloring agents include all dyes and lakes approved by the U.S. Food and Drug Administration (e.g., FD&C colorants).

In some embodiments, sweetening agents may be used to mask unpleasant taste or to achieve a desired taste. Examples of sweetening agents are glucose, sorbitol, glycerol, acesulfame potassium and neohesperidin dihydrochalcon. The taste may be optimized further by the addition of one or more flavoring substances. Suitable flavoring substances are fruit flavors such as cherry, raspberry, black currant, lemon or strawberry flavor or other flavors such as liquorice, anise, peppermint, and caramel.

The solid dosage forms of the present disclosure may be prepared by, for example, wet granulating lumateperone, in free or pharmaceutically acceptable salt form, and one or more pharmaceutically acceptable carriers or diluents (i.e., excipients), for example, a binder and/or a disintegrant with water or a binder solution, using a machine such as a high speed mixer granulator, a fluidized-bed granulator dryer, a centrifugal tumbling fluidized-bed granulator coating machine or a kneading machine; blending or spraying a lubricant to the granules; and then subjecting to compression molding. Alternatively, the solid dosage forms of the present disclosure can be prepared by dry granulating lumateperone, in free or pharmaceutically acceptable salt form, and one or more pharmaceutically acceptable carriers or diluents (i.e., excipients), for example, a binder (a disintegrant may be further contained), using a machine such as a roller compactor; blending or spraying a disintegrant (a lubricant may be further contained) to the granules; and then subjecting to compression molding.

Suitable forms of lumateperone include the free base form, including amorphous solid dispersions thereof, pharmaceutically acceptable salt forms, including amorphous solid dispersions and crystal forms thereof, and pharmaceutically acceptable co-crystal forms. Amorphous solid dispersion forms of lumateperone free base are disclosed in patent publication WO 2018/71233, and related applications thereto, the contents of which are hereby incorporated by reference in their entireties.

Unless otherwise indicated, the term "pharmaceutically acceptable salt" includes acid addition salts between lumateperone and any pharmaceutically acceptable acid (e.g., Bronsted acid) in any molar ratio permitted by the structure of the acid. For example, "pharmaceutically acceptable salt form" of lumateperone includes the mono-hydrochloride, the di-hydrochloride, the tri-hydrochloride, the mono-tosylate, the di-tosylate and the tri-tosylate, or any mixtures thereof. In some embodiments, the lumateperone salt is a crystalline solid (e.g., a salt crystal). In some embodiments, the lumateperone may exist as a co-crystal, i.e., lumateperone free base co-crystallized with a second species. Pharmaceutically acceptable salt and co-crystal forms of lumateperone include all those forms disclosed in U.S. Pat. Nos. 8,648,077, 9,199,995, and 9,586,960, and patent publications WO 2017/1172811 and WO 2017/172784, and U.S. provisional applications 62/563,341 and 62/681,534, the contents of each of which are hereby incorporated by reference in their entireties.

In a second aspect, the present disclosure provides a process (Process 1) for the manufacture of Dosage Form 1, or any of 1.1-1.49, wherein the process comprises the steps of:
(a) combining lumateperone, in free or pharmaceutically acceptable salt form (e.g., tosylate salt form), with at least one diluent or carrier (e.g., with a filler, such as mannitol);
(b) blending and/or milling and/or granulating (e.g., dry granulating) the resulting the mixture;
(c) optionally filtering (e.g., screening) the resulting mixture, e.g., to achieve a uniform particle size;
(d) adding at least one other diluent or carrier (e.g., a disintegrant (e.g., croscarmellose sodium), or a glidant (e.g., talc), or a lubricant (e.g., magnesium stearate), or a combination thereof);
(e) blending and/or milling and/or granulating (e.g., dry granulating) the resulting mixture;
(f) optionally filtering (e.g. screening) the resulting mixture, e.g., to achieve a uniform particle size;
(g) pressing the mixture to form the Dosage Form;
(h) optionally applying one or more coatings to the Dosage Form.

It is understood that in embodiments of the present disclosure wherein lumateperone is provided in the form of an amorphous solid dispersion (either of lumateperone free base or lumateperone tosylate), that in step (a) of Process 1 it is the dispersion that is combined with at least one further diluent or carrier. As such, the amorphous solid dispersion would be prepared in a step antecedent to step (a) by combining the lumateperone and any excipients necessary to form the solid dispersion thereof.

In some embodiments, steps (d), (e), and/or (f) may be repeated for additional diluents or carriers. For example, the process steps may comprise steps (a), (b), (c), (d1), (e1), (f1), (d2), (e2), (f2), (g), and (h). The steps (d), (e), and (f) may be repeated any number of times to provide for the additional addition, blending/milling and/or filtering of any individual ingredients or portions of ingredients in order to optimize process flow. Thus, for example, in some embodiments, the binder components may be added in two or three portions, such as in steps (a), (d1) and (d2), or the lubricant may be added in a final addition step (e.g., step (d2)). In some embodiments, the process optionally further includes one or more dry granulation steps (e.g., roller compaction or slugging) which serve to increase the size of solid particles from powder-scale to granule-scale. In some embodiments, one or more blending steps may further include running the blend through a roller compactor, and optionally then milling the roller compacter ribbons. In some embodiments, any dry granulation step may be followed by a blending step to blend the resulting granules with one or more other excipients (e.g., lubricant).

In some embodiments, the final step of coating the Dosage Form is performed by suspending the un-coated Dosage Form in an aqueous suspension of coating polymer followed by drying to remove the water and any co-solvents. Optionally, the coating is applied at high temperature and/or the coated tablets are dried at high temperature (e.g., 40 to 60° C.). In some embodiments, the coating is applied by spraying an aqueous suspension of the coating polymer onto uncoated Dosage Form, followed by drying.

In a third aspect, the present disclosure provides a method (Method 1) for the treatment or prophylaxis of a disease or disorder involving or mediated by the 5-HT2A receptor, serotonin transporter (SERT), and/or dopamine D1/D2 receptor signaling pathways, comprising administering to a patient in need thereof the solid dosage form according to Dosage Form 1 or any of 1.1-1.49. In some embodiments, said disease or disorder is selected from obesity, anorexia, bulimia, depression (including major depressive disorder (MDD), acute depression, post-traumatic depression), anxiety (including acute anxiety, panic disorders, phobias, social anxiety disorder, or social withdrawal), psychosis (including acute psychosis), schizophrenia (including residual symptoms of schizophrenia, such as positive and/or negative symptoms of schizophrenia), obsessive-compulsive disorder, sexual disorders, migraine, attention deficit disorder, attention deficit hyperactivity disorder, sleep disorders, conditions associated with cephalic pain, anger disorders, agitation (including acute agitation), dementia (including Alzheimer's Disease and Parkinson's dementia), gastrointestinal disorders such as dysfunction of gastrointestinal tract motility, and bipolar disorder (e.g., bipolar depression).

The words "treatment" and "treating" are to be understood accordingly as embracing prophylaxis and treatment or amelioration of symptoms of disease and/or treatment of the cause of the disease. In particular embodiments, the words "treatment" and "treating" refer to prophylaxis or amelioration of symptoms of the disease.

The term "patient" may include a human or non-human patient.

Methods of synthesizing lumateperone and related compounds are known in art, and include the methods disclosed in WO PCT/US08/03340 (WO 2008/112280); U.S. application Ser. No. 10/786,935; U.S. Pat. Nos. 6,548,493; 7,238,690; 6,552,017; 6,713,471; 7,183,282; 8,309,722; 8,779,139; 9,315,504; U.S. RE39680, and U.S. RE39679, and WO 2015/154025, the contents of each of which are incorporated by reference in their entirety. Salts of the Compounds of the Invention may also be prepared as similarly described in U.S. Pat. Nos. 6,548,493; 7,238,690; 6,552,017; 6,713,471; 7,183,282, 8,648,077; 9,199,995; 9,588,960; U.S. RE39680; U.S. RE39679; and WO 2009/114181, the contents of each of which are incorporated by reference in their entirety.

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

The pharmaceutically acceptable salts of lumateperone can be synthesized from the parent compound, which contains basic moieties, by reaction with a suitable acid, by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred.

Dosages employed in practicing the present disclosure will of course vary depending, e.g. on the particular disease or condition to be treated, the particular active compounds used, the mode of administration, and the therapy desired. Unless otherwise indicated, an amount of an active compound for administration (whether administered as a free base or as a salt form) refers to or is based on the amount of the compound in free form (i.e., the calculation of the amount is based on the amount of active moiety in free form, not taking into account the weight of the counter ion in the case of a salt).

For the avoidance of doubt, any disclosure of a numerical range, e.g., "up to X" amount is intended to include the upper numerical limit X. Therefore, a disclosure of "up to 60 mg" is intended to include 60 mg.

Example 1: Excipient Compatibility Study

The chemical compatibility of lumateperone monotosylate with selected excipients is studied. Excipients evaluated are (1) Fillers (silicified microcrystalline cellulose, and lactose monohydrate); (2) Disintegrants (sodium starch glycolate); (3) Binders (pregelatinized starch, hydroxypropyl cellulose, hydroxypropyl methyl cellulose, and copovidone); and (4) Coating Polymers (polyvinyl alcohol-based film coating comprising PVA, titanium dioxide and talc). Lumateperone tosylate is mixed in a 1:1 weight ratio with each excipient and the mixture is evaluated (1) immediately after mixing, (2) after 4, 8 and 12 weeks of aging at 25° C. and 60% relative humidity, and (3) after 4, 8 and 12 weeks of accelerated aging at 40° C. and 75% relative humidity. Comparisons are made to lumateperone tosylate under the same conditions without excipient. Potency, appearance, moisture content and related substances levels are evaluated. It is found that there are no chemical incompatibilities with the selected excipients. All potency measurements of the binary mixtures show lumateperone tosylate levels comparable to the control. Under the accelerated aging conditions, slight decreases in potency are observed for both the control (90.9-93.5% potency over 4-12 weeks) and the binary mixtures, and this is believed due to air oxidation of the lumateperone tosylate. Slight increase in moisture content are observed for samples in the accelerated aging arm, with larger increases for the more hydroscopic excipients (e.g., pregelatinized starch). Related substance levels are acceptable for all binary mixtures analyzed.

Example 2: Tablet Development Process 14 mg, 28 mg, and 42 mg immediate-release film-coated tablets of lumateperone monotosylate are prepared according to the formulae shown in the tables below. Batches are prepared on a multi-kilogram scale, and each batch is prepared in three different runs:

| Ingredient | 14 mg Batch |
|---|---|
| Lumateperone tosylate | 7.6 wt % |
| Silicified microcrystalline cellulose (SMCC) | 60 wt % |
| Mannitol | 19 wt % |
| Hydroxypropyl cellulose | 3 wt % |
| Croscarmellose sodium | 3 wt % |
| BHT | 0.8 wt % |
| Colloidal silicon dioxide | 0.4 wt % |
| Magnesium stearate | 1 wt % |
| PVA Coating | 4.8 wt % |
| Common Blend | 95 wt % |
| PVA Coating | 5 wt % |

| Ingredient | 28/42 mg Batch Common Blend | |
|---|---|---|
| Lumateperone tosylate | 16 wt % | |
| SMCC | 55 wt % | |
| Mannitol | 20 wt % | |
| Hydroxypropyl cellulose | 3.2 wt % | |
| Croscarmellose sodium | 3.2 wt % | |
| BHT | 0.8 wt % | |
| Colloidal silicon dioxide | 0.4 wt % | |
| Magnesium stearate | 1 wt % | |
| | 28 mg Batch | 42 mg Batch |
| Common Blend | 95 wt % | 95 wt % |
| PVA Coating | 5 wt % | 5 wt % |

For 14 mg tablets, mannitol, silicon dioxide, BHT, and lumateperone tosylate are combined in a 3-cubic foot V-blender and mixed for 5 minutes at 25 rpm. A first portion of the microcrystalline cellulose is then added, and the mixture is blended for 5 additional minutes. The blended mixture is passed through a Comil brand conical mill with a round impeller using a 1.6 mm aperture screen and milled/screened. A second portion of cellulose is milled and then combined with the milled blend and a third portion of cellulose, and the mixture is blended for 10 minutes at 25 rpm. The HPMC and croscarmellose sodium portions are pre-screened through a 20-mesh screen, then added to the blended mixture and the further blended for 5 minutes at 25 rpm. Finally, the magnesium stearate portion is pre-screened through a 30-mesh screen, added to the blended mixture, and the mixture is further blended for 3 minutes at 25 rpm.

The common blend for 28 mg and 42 mg tablets is prepared analogously using a 10 cubic foot V-blender, operated at a reduced speed of 20.5 rpm, with similar blending times.

For both the 14 mg and 28/42 mg blends, blend uniformity and physical properties are evaluated by taking samples from throughout the blender at the time final blending is stopped (10 locations are each sampled for each V-blender). Mean blend uniformity is found to be about 97% for the 14 mg batch and about 96% for the common blend batch over all three runs of each batch. Physical properties, including particle size distribution, bulk density, tapped density, and flow, are found to be highly consistent between the three runs of each batch.

0.1N aqueous hydrochloric acid as the dissolution media. The results (batch means) are shown in the table below for 14 mg and 42 mg tablets. Results for 28 mg tablets are comparable.

|  | Batch | | | | | |
|---|---|---|---|---|---|---|
|  | 14 mg tablets | | | 42 mg tablets | | |
|  | 1 | 2 | 3 | 1 | 2 | 3 |
| Dissolution (%) at 15 min | 86 | 90 | 93 | 86 | 81 | 83 |
| Dissolution (%) at 30 min | 95 | 96 | 99 | 96 | 92 | 93 |
| Dissolution (%) at 45 min | 98 | 97 | 100 | 100 | 98 | 98 |
| Dissolution (%) at 60 min | 98 | 98 | 100 | 101 | 100 | 99 |
| Uniformity (%) [USP 905] | 99.8 | 100.4 | 99.7 | 100.7 | 100.2 | 98.9 |
| Assay (%) | 98 | 99 | 98 | 100 | 99 | 99 |

Example 3: Alternative Tablet Formulation and Process

Alternative, anti-oxidant free, tablet formulations are prepared according to the formulas shown below for 14-mg, 28-mg and 42-mg tablets:

| Ingredient | 14 mg* Tablets | | 28 mg* Tablets | | 42 mg* Tablets | |
|---|---|---|---|---|---|---|
|  | Weight % | Weight (mg) | Weight % | Weight (mg) | Weight % | Weight (mg) |
| Lumateperone tosylate | 8.0 | 20.0 | 16.0 | 40.0 | 16.0 | 60.0 |
| SMCC (e.g., Prosolv HD 90) | 64.2 | 160.5 | 56.2 | 140.5 | 56.2 | 210.75 |
| Mannitol | 20.0 | 50.0 | 20.0 | 50.0 | 20.0 | 75.0 |
| Hydroxypropyl cellulose | 3.2 | 8.0 | 3.2 | 8.0 | 3.2 | 12.0 |
| Croscarmellose sodium | 3.2 | 8.0 | 3.2 | 8.0 | 3.2 | 12.0 |
| Colloidal Silicon Dioxide | 0.4 | 1.0 | 0.4 | 1.0 | 0.4 | 1.5 |
| Magnesium Stearate | 1.0 | 2.5 | 1.0 | 2.5 | 1.0 | 3.75 |
| TOTAL | 100% | 250 | 100% | 250 | 100% | 375 |

*equivalent weight of lumateperone free base in each tablet

From each batch, tablets are prepared using a commercial tablet press using 0.2000 inch by 0.4758-inch modified capsule embossed B tooling and tapered dies. Target weight for the 14 mg and 28 mg tablets is 250 mg, and for the 42 mg tablets 375 mg. All batches are compressed using force feed frame. Compression parameters and compression yields are evaluated for each batch run, including average tablet weight, hardness, thickness, friability, and disintegration time. All parameters are found to be compliant and consistent between the batch runs.

Tablets are then coated using a commercial multi-pan laboratory coating system using a 30-inch pan. Each batch is coated with a target weight of 5 wt % coating, using a commercial, aqueous polyvinyl alcohol coating suspension comprising 20 wt % solids, using two anti-bearding guns equipped with 1.2 mm nozzles. The coating suspension is mixed for 45 minutes in a stainless-steel tank and then allowed to de-aerate for at least 60 minutes prior to use. Target coating parameters are based on the manufacturer's guidelines. The coating process is found to be acceptable.

The coated tablets from each batch run are then tested in standard dissolution and other analytical assays. Each batch is tested in a standard dissolution study using 500 mL of 14 mg and 28 mg tablets are each coated with 12.5 mg of PVA coating (5 wt % of core weight), while 42 mg tablets are coated with 18.75 mg of PVA coating (5 wt % of core weight).

Tablets are prepared, as shown in the above table, in 14 mg, 28 mg and 42 mg sizes (free base equivalent; corresponding to 20 mg, 40 mg, or 60 mg, respectively, of lumateperone tosylate). The procedure for preparing the tablets is as follows (amounts in parentheses are with reference to the total amount of indicated ingredient in the composition):

a. Mannitol (e.g., 50%) is added to a V-blender and is blended;
b. Lumateperone tosylate (100%) and additional mannitol (e.g., 50%) are added to the V-blender and blended;
c. SMCC (e.g., 40%) is added to the V-blender, and blended;
d. The preblend from step (c) is milled in a Comil conical mill; additional SMCC (e.g., 40%) is also milled in the Comil;
e. The milled materials from step (d) are returned to the V-blender and blended;

f. Croscarmellose sodium (e.g., 50%), HPC (e.g., 50%), and silicon dioxide (e.g., 50%) are added to the V-blender and blended;

g. Magnesium stearate (e.g., 50%) is added to the v-blender and blended;

h. The blend from step (g) is run through a roller compactor and milled to create granules;

i. The granules from step (h) are returned to the V-blender, additional croscarmellose sodium (e.g., 50%) and HPC (e.g., 50%) are added, and the mixture is blended;

j. Additional SMCC (e.g., 20%) is added to the v-blender and blended;

k. Additional magnesium stearate (e.g., 50%) is added to the v-blender and blended;

l. The blend is compressed to form tablets on a rotary tablet press;

m. The tablets are coated in a perforated coating pan.

Tablets prepared according to the above formulas are packaged in blister packs comprising PVC/PE/PCTFE film and 20-micron aluminum foil (peel-push). The packaged tablets are tested for stability using standard procedures. Tested conditions are (1) initial, (2) 50° C./ambient humidity for 1-3 months, (3) 40° C./75% relative humidity for 1-3 months, and (4) 25° C./60% relative humidity for 1 month. Tablets are assayed using reverse-phase HPLC for lumateperone tosylate content, as well as for known impurities. Tablets are also subject to a standard dissolution test (dissolution in 500 mL 0.1N aqueous hydrochloric acid). The results (batch means) are shown in the table below:

|  | Initial | 3 mo. 50° C./ amb RH | 3 mo. 40° C./ 75% RH | 1 mo. 25° C./ 60% RH |
|---|---|---|---|---|
| 28 mg Tablets | | | | |
| Assay (% of label claimed amount) | 100.0% | 98.8% | 97.9% | 99.8% |
| Net Related Substance Impurities (max single) | 0.28% (0.15%) | 0.97% (0.22%) | 1.1% (0.24%) | 0.34% (0.17%) |
| R.S. Impurities Detectable (Quantifiable) | 4 (2) | 9 (6) | 14 (6) | 4 (2) |
| Dissolution (%) at 15 min | 76% | 83% | 78% | 79% |
| Dissolution (%) at 30 min | 90% | 94% | 90% | 91% |
| Dissolution (%) at 45 min | 99% | 99% | 97% | 97% |
| Dissolution (%) at 60 min | 104% | 100% | 99% | 101% |
| Moisture (%) [USP 921] | 2.6% | 1.2% | 3.0% | 2.5% |
| 14 mg Tablets | | | | |
| Assay (% of label claimed amount) | 100.0% | 97.9% | 95.6% | 100.0% |
| Net Related Substance Impurities (max single) | 0.44% (0.17%) | 1.5% (0.29%) | 2.3% (0.31%) | 0.49% (0.21%) |
| R.S. Impurities Detectable (Quantifiable) | 3 (3) | 12 (7) | 24 (12) | 5 (3) |
| Dissolution (%) at 15 min | 81% | 95% | 82% | 90% |
| Dissolution (%) at 30 min | 90% | 101% | 95% | 99% |
| Dissolution (%) at 45 min | 92% | 103% | 99% | 101% |
| Dissolution (%) at 60 min | 92% | 103% | 100% | 102% |
| Moisture (%) [USP 921] | 2.8% | 1.3% | 3.4% | 2.8% |
| 42 mg Tablets | | | | |
| Assay (% of label claimed amount) | 100.8% | 98.9% | 97.5% | 100.4% |
| Net Related Substance Impurities (max single) | 0.25% (0.15%) | 1.1% (0.27%) | 1.3% (0.28%) | 0.40% (0.16%) |
| R.S. Impurities Detectable (Quantifiable) | 4 (2) | 12 (6) | 19 (7) | 6 (3) |
| Dissolution (%) at 15 min | 82% | 85% | 73% | 79% |
| Dissolution (%) at 30 min | 92% | 94% | 86% | 95% |
| Dissolution (%) at 45 min | 96% | 98% | 93% | 100% |
| Dissolution (%) at 60 min | 97% | 99% | 96% | 101% |
| Moisture (%) [USP 921] | 2.6% | 1.3% | 3.1% | 2.7% |

The lumateperone assay FIGURE is a reflection of the accuracy of the label claim, as it is presented as a percentage of the label amount (e.g., 14-mg, 28-mg or 42-mg) rather than as a percentage of the tablet composition. Acceptance of a batch requires that the batch of tablets is measured to have a mean of 90.0-110.0% of the claimed label amount of active drug.

The FIGURE for Net Related Substance Impurities indicates the percentage of all related substance impurities in the composition (as judged by HPLC peak area). Parenthetically provided is the highest percentage of any single impurity detected. Acceptance of a batch requires that total related substance impurities amount to not more than 3.0%, with no single related substance impurity amounting to more than 0.5%.

The Quantifiable R.S. (Related Substances) Impurities FIGURE is the number of distinct detectable HPLC peaks associated with related substance impurities, while the parenthetical FIGURE is for the number of such peaks above the lower limit of quantifiability. For all conditions reported in the table above, no single impurity exceeded the 0.5% acceptance limit.

The presence of increasing amounts of impurities during the test conditions reflects instability of the active ingredient, as does a drop in the Assay FIGURE. The data demonstrates that the tablets formulated according to the invention have acceptable physical and chemical stability based on all measured tested.

Example 4: Alternative Anti-Oxidants

A study is conducted to evaluate the effectiveness of the anti-oxidants propyl gallate, ascorbic acid, citric acid (anhydrous) and sodium metabisulfite. Each antioxidant is combined with either lumateperone tosylate (pure API) or with the lumateperone tosylate tablet formulation final blend of Example 3 (not pressed into tablets) in various weight ratios in amber scintillation vials. In addition, as controls, one vial holds lumateperone tosylate API and another holds the lumateperone tosylate tablet formulation final blend (42 mg strength). All vials are then stored at 60° C. for 2 weeks, 4 weeks, or 8 weeks, after which the vial contents are tested for physical appearance, HPLC potency and HPLC impurities (related substances/degradation products). The samples can be summarized as follows:

| Sample | Active | | Anti-oxidant | |
|---|---|---|---|---|
| 1 | Lumateperone blend | 2250 mg | — | 0 |
| 2 | Lumateperone API | 362 mg | — | 0 |
| 3 | — | 0 | Propyl Gallate | 8.16 mg |
| 4 | — | 0 | Ascorbic Acid | 170.6 mg |
| 5 | — | 0 | Citric Acid (anhyd.) | 122.4 mg |
| 6 | — | 0 | Sodium metabisulfite | 48 mg |
| 7 | Lumateperone API | 362 | Propyl Gallate | 8.16 mg |
| 8 | Lumateperone API | 362 | Ascorbic Acid | 170.6 mg |
| 9 | Lumateperone API | 362 | Citric Acid (anhyd.) | 122.4 mg |
| 10 | Lumateperone API | 362 | Sodium metabisulfite | 48 mg |
| 11 | Lumateperone blend | 2250 mg | Propyl Gallate | 8.16 mg |
| 12 | Lumateperone blend | 2250 mg | Ascorbic Acid | 170.6 mg |
| 13 | Lumateperone blend | 2250 mg | Citric Acid (anhyd.) | 122.4 mg |
| 14 | Lumateperone blend | 2250 mg | Ascorbic Acid | 85.3 mg |

-continued

| Sample | Active | | Anti-oxidant | |
|---|---|---|---|---|
| 15 | Lumateperone blend | 2250 mg | Citric Acid (anhyd.) | 61.2 mg |
| 16 | Lumateperone blend | 2250 mg | Sodium metabisulfite | 24 mg |

The following table provides the result of the study at 8-weeks:

| Sample | Appearance | Assay (%) | RS Impurities (%) Known | RS Impurities (%) Unknown | Mass Bal. |
|---|---|---|---|---|---|
| 1 | Original (off-white powder) | 95.7 | 0.61 | 0.93 | 97.2 |
| 2 | Granules present | 99.7 | 0.36 | None | 100.0 |
| 7 | Black residue and granules | 95.5 | 0.65 | 1.1 | 97.3 |
| 8 | Original | 99.8 | 0.42 | none | 100.2 |
| 9 | Dark lumps present | 95.5 | 0.62 | 0.59 | 96.7 |
| 10 | Granules present | 98.6 | 0.44 | 0.14 | 99.2 |
| 11 | Black particles present | 94.6 | 0.57 | 1.1 | 96.3 |
| 12 | Original | 96.4 | 0.60 | 0.36 | 97.4 |
| 13 | Black granules present | 96.8 | 0.59 | 0.60 | 98.0 |
| 14 | Original | 96.8 | 0.60 | 1.0 | 98.4 |
| 15 | Dark lumps present | 95.8 | 0.56 | 0.73 | 97.1 |
| 16 | Grey powder | 86.8 | 0.64 | 1.6 | 80.7 |

The results of the study are summarized as follows:

a. Both controls remain off-white powders through 8 weeks, although pure API formed some granules by 8 weeks. Pure API retains full potency at 8 weeks (99.7%), while the blend (without antioxidant) drops from 100.0% to 95.7% potency at 8 weeks.

b. Ascorbic acid is the only anti-oxidant which maintained full physical stability (appearance unchanged) at 8 weeks, and it was effective both for lumateperone tosylate API and for the blend formula. Sodium metabisulfite was substantially unchanged at 8 weeks when mixed with API (some granules formed), but mixed with the blend the powder changed to a grey color.

c. Ascorbic acid mixed with API retained full chemical potency, but the other anti-oxidants resulted in a drop in pure API potency (from 99.7% to 95.5-98.6%).

d. At both weight ratios, ascorbic acid mixed with the blend retained >95.7% potency, as did citric acid, but the other anti-oxidants mixed with the blend resulted in <95.7% potency at 8 weeks (and thus less than blend without antioxidants). In addition, for both ascorbic acid and citric acid mixed with blend, after 8 weeks, known and known related substances impurities were comparable to or better than the blend alone.

Overall, the study suggests that ascorbic acid is a preferred anti-oxidant for maintaining physical and chemical stability of lumateperone tosylate in a tablet formulation blend.

We claim:
1. A solid oral dosage form, comprising lumateperone:

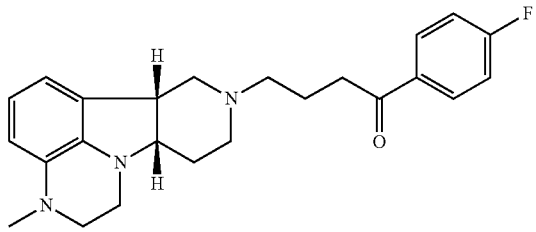 [SMILES: CN1CCN2c3c(cccc31)[C@@H]1CN(CCCC(=O)c3ccc(F)cc3)CC[C@@H]12]

wherein the dosage form is an immediate release dosage form;
wherein the dosage form is a tablet formulated for oral (gastrointestinal) administration;
wherein the dosage form comprises the lumateperone in mono-tosylate salt form;
wherein the lumateperone mono-tosylate is in solid crystal form; and
wherein the composition further comprises one or more pharmaceutically acceptable diluents or carriers comprising at least:
(a) 60-90% by weight of a diluent/filler selected from cellulose, microcrystalline cellulose, mannitol, lactose monohydrate, dicalcium phosphate, and isomalt,
(b) 1-10% by weight of a binder selected from hydroxypropyl cellulose, hydroxypropyl methyl cellulose, and copovidone,
(c) 1-10% by weight of a disintegrant selected from sodium starch glycolate, crospovidone, and croscarmellose sodium,
(d) 0.1-5% by weight of a lubricant selected from magnesium stearate and glyceryl monostearate, and
(e) 0.1-5% by weight of a glidant selected from silicon dioxide and talc.

2. The dosage form of claim 1, wherein the dosage form further comprises lumateperone in di-tosylate salt form.

3. The dosage form of claim 1, wherein the lumateperone mono-tosylate solid crystal form exhibits an X-ray powder diffraction pattern comprising at least two peaks having 2-theta values selected from the group consisting of 5.68°, 12.11°, 16.04°, 17.03°, 18.16°, 19.00°, 21.67°, 22.55°, 23.48° and 24.30°, each of said peaks ±0.2°, wherein the X-ray powder diffraction data is collected on a diffractometer operating with a copper anode with a nickel filter.

4. The dosage form of claim 1, wherein the dosage form further comprises toluenesulfonic acid.

5. The dosage form of claim 1, wherein the dosage form comprises the lumateperone mono-tosylate in a total unit amount equivalent to 0.01 to 120 mg of lumateperone free base.

6. The dosage form of claim 1, wherein the one or more pharmaceutically acceptable diluents or carriers further comprises one or more of (f) effervescent, (g) polymer, (h) plasticizer, (i) drying agent or desiccant, (j) humectant, (k) wetting agent, (l) anti-oxidant, (m) thickening agent, (n) surfactant, (o) buffer, (p) sweetener or flavor, and (q) dye or colorant.

7. The dosage form of claim 1, wherein the dosage form comprises or consists of (a) lumateperone mono-tosylate, lactose monohydrate, starch, cellulose, hydroxypropyl cellulose (HPC), hydroxypropyl methyl cellulose (HPMC), copovidone (cross-linked polyvinyl pyrrolidone), sodium starch glycolate, flavors and/or colors and/or antioxidants, or (b) lumateperone mono-tosylate, cellulose, hydroxypropyl cellulose (HPC), croscarmellose sodium (cross-linked carboxymethyl cellulose sodium), silicon dioxide, magnesium stearate, flavor and/or colors and/or antioxidants.

8. The dosage form of claim 1, wherein the dosage form comprises one or more surface coatings.

9. The dosage form of claim 1, wherein the dosage form is a spherical or approximately spherical, oval or oblong tablet, or is a caplet.

10. The dosage form of claim 1, wherein the lumateperone mono-tosylate is in the form of paricles having (a) a mean particle size of 1 to 200 μm, 1 to 150 μm, 1 to 100 μm, 1 to 50 μm, 1 to 25 μm, 1 to 15 μm, 1 to 10 μm, 5 to 10 μm, or 1 to 5 μm; and/or (b) a D90 of 100 μm or less, 50 μm or less, 25 μm or less, 15 μm or less, or 10 μm or less; and/or (c) a D10 of 50 μm or less, 25 μm or less, 15 μm or less, or 10 μm or less, or 5 μm or less.

11. The dosage form of claim 1, wherein the lumateperone is in combination with an effective amount of an additional therapeutic agent.

12. A process for the manufacture of the dosage form according to claim 1, wherein the process comprises the steps of:
    (a) combining lumateperone mono-tosylate, with at least one diluent or carrier;
    (b) blending and/or milling and/or granulating the resulting the mixture;
    (c) optionally filtering the resulting mixture to achieve a uniform particle size;
    (d) adding at least one other diluent or carrier, or a glidant, or a lubricant, or a combination thereof;
    (e) blending and/or milling and/or granulating the resulting mixture;
    (f) optionally filtering the resulting mixture to achieve a uniform particle size;
    (g) pressing the mixture to form the dosage form; and
    (h) optionally applying one or more coating to the dosage form.

13. A method for the treatment or prophylaxis of a disease or disorder involving or mediated by the 5-HT2A receptor, serotonin transporter (SERT), and/or dopamine D1/D2 receptor signaling pathways, comprising administering to a patient in need thereof the solid dosage form according to claim 1.

14. The dosage form of claim 1, wherein the dosage form comprises silicified microcrystalline cellulose, mannitol, hydroxypropyl cellulose, croscarmellose sodium, magnesium stearate, and silicon dioxide.

15. The dosage form of claim 14, wherein the dosage form comprises 60-90% by weight of microcrystalline cellulose and mannitol, 1-10% by weight of hydroxypropyl cellulose, 1-10% by weight of croscarmellose sodium, 0.1-5% by weight of magnesium stearate, and 0.1-5% by weight of silicon dioxide.

16. The dosage form of claim 15, wherein the dosage form comprises the lumateperone mono-tosylate in a total unit amount equivalent to 1 to 60 mg of lumateperone free base.

17. The dosage form of claim 1, wherein the dosage form comprises the lumateperone mono-tosylate in a total unit amount equivalent to 1 to 60 mg of lumateperone free base.

* * * * *